(12) United States Patent
McCormack (10) Patent No.: US 11,703,393 B2
(45) Date of Patent: Jul. 18, 2023

(54) SYSTEM AND METHOD FOR MONITORING COOLING SYSTEM

(71) Applicant: SOUTHWEST MEDICAL RESOURCES, INC., Ontario, CA (US)

(72) Inventor: Michael Shane McCormack, Corona, CA (US)

(73) Assignee: Southwest Medical Resources, Inc., Fontana, CA (US)

( * ) Notice: Subject to any disclaimer, the term of this patent is extended or adjusted under 35 U.S.C. 154(b) by 827 days.

(21) Appl. No.: 16/428,825

(22) Filed: May 31, 2019

(65) Prior Publication Data

US 2019/0368945 A1     Dec. 5, 2019

Related U.S. Application Data

(60) Provisional application No. 62/679,701, filed on Jun. 1, 2018.

(51) Int. Cl.
| | |
|---|---|
| *G01K 3/14* | (2006.01) |
| *G01R 33/38* | (2006.01) |
| *G01R 33/3815* | (2006.01) |
| *A61B 5/055* | (2006.01) |
| *G01K 1/02* | (2021.01) |
| *G01K 13/02* | (2021.01) |
| *G01K 17/12* | (2006.01) |

(52) U.S. Cl.
CPC ............ *G01K 3/14* (2013.01); *A61B 5/055* (2013.01); *G01K 1/026* (2013.01); *G01K 13/02* (2013.01); *G01K 17/12* (2013.01); *G01R 33/3804* (2013.01); *G01R 33/3815* (2013.01)

(58) Field of Classification Search
CPC .......... G01K 3/14; G01K 1/026; G01K 13/02; G01K 17/12; A61B 5/055; G01R 33/3804; G01R 33/3815
See application file for complete search history.

(56) References Cited

U.S. PATENT DOCUMENTS

| | | | | |
|---|---|---|---|---|
| 5,960,636 | A * | 10/1999 | Schuck | G01R 33/3804 |
| | | | | 62/332 |
| 6,252,405 | B1 * | 6/2001 | Watkins | G01R 33/389 |
| | | | | 324/319 |
| 6,354,087 | B1 * | 3/2002 | Nakahara | H02G 15/34 |
| | | | | 62/6 |
| 6,516,282 | B2 * | 2/2003 | Hedlund | G01R 33/3856 |
| | | | | 702/132 |
| 6,525,537 | B2 * | 2/2003 | Nerreter | G01R 33/3856 |
| | | | | 324/318 |
| 6,655,835 | B2 * | 12/2003 | Mattoon | G01K 1/026 |
| | | | | 374/E1.005 |
| 6,909,283 | B2 * | 6/2005 | Emeric | G01R 33/3856 |
| | | | | 324/306 |

(Continued)

*Primary Examiner* — Lisa M Caputo
*Assistant Examiner* — Philip L Cotey
(74) *Attorney, Agent, or Firm* — Lewis Roca Rothgerber Christie LLP (57) ABSTRACT

An apparatus for monitoring a cooling system. In some embodiments, the cooling system includes a chiller and a heat exchange process connected to the chiller by a coolant supply line and a coolant return line, and the apparatus includes a first temperature sensor, for measuring a coolant temperature in the coolant supply line, and a second temperature sensor, for measuring a coolant temperature in the coolant return line.

15 Claims, 4 Drawing Sheets

(56) References Cited

U.S. PATENT DOCUMENTS

| | | | | |
|---|---|---|---|---|
| 6,992,483 B1* | 1/2006 | Emeric | G01R 33/3856 | 324/306 |
| 7,297,907 B2 | 11/2007 | Rapoport et al. | | |
| 7,301,343 B1* | 11/2007 | Sellers | G01R 33/28 | 324/318 |
| 7,304,477 B2* | 12/2007 | Konijn | F16F 15/02 | 324/318 |
| 7,511,501 B2* | 3/2009 | Wexler | G01R 33/4215 | 324/318 |
| 7,538,551 B2* | 5/2009 | Kimmlingen | G01R 33/3856 | 324/318 |
| 7,602,185 B2* | 10/2009 | Nozaki | G01R 33/3856 | 324/309 |
| 7,868,617 B2* | 1/2011 | Seeber | G01R 33/3815 | 324/318 |
| 7,994,787 B2* | 8/2011 | Tsuda | G01R 33/3806 | 324/309 |
| 8,102,178 B2* | 1/2012 | Stocker | G01T 1/362 | 324/318 |
| 8,188,741 B2* | 5/2012 | Sakakura | G01R 33/3856 | 324/318 |
| 8,305,079 B2* | 11/2012 | Iwasa | G01R 33/3804 | 324/318 |
| 8,564,292 B2* | 10/2013 | Iwasa | G01R 33/3856 | 324/318 |
| 8,593,145 B2* | 11/2013 | Van Der Koijk | G01R 33/58 | 324/318 |
| 8,602,049 B2* | 12/2013 | Lose | G01R 33/3804 | 222/61 |
| 8,643,370 B2* | 2/2014 | Kimmlingen | G01R 33/3856 | 324/318 |
| 8,680,862 B2* | 3/2014 | Yamashita | G01R 33/3856 | 324/318 |
| 9,810,754 B2* | 11/2017 | Tanaka | G01R 33/3804 | |
| 10,047,977 B2* | 8/2018 | Hamasaki | F25B 49/005 | |
| 10,267,876 B2* | 4/2019 | Kreischer | G01R 33/3856 | |
| 2003/0052681 A1* | 3/2003 | Kono | G01R 33/3815 | 324/318 |
| 2003/0140638 A1* | 7/2003 | Arshansky | F25D 17/02 | 62/278 |
| 2004/0017195 A1* | 1/2004 | Kassai | G01R 33/3856 | 324/315 |
| 2005/0035764 A1* | 2/2005 | Mantone | G01R 33/3856 | 324/309 |
| 2005/0126276 A1* | 6/2005 | Chu | H05K 7/2079 | 73/149 |
| 2007/0125102 A1* | 6/2007 | Concha | G01K 13/02 | 62/149 |
| 2009/0015258 A1* | 1/2009 | Nozaki | G01R 33/3856 | 324/315 |
| 2009/0123139 A1* | 5/2009 | Seeber | G01R 33/389 | 392/416 |
| 2009/0128269 A1* | 5/2009 | Seeber | G01R 33/389 | 324/318 |
| 2010/0016168 A1* | 1/2010 | Atkins | F25D 3/105 | 62/48.1 |
| 2010/0188083 A1* | 7/2010 | Cao | G01R 33/389 | 324/318 |
| 2010/0315086 A1* | 12/2010 | Sakakura | G01R 33/3856 | 324/318 |
| 2013/0287063 A1* | 10/2013 | Kates | G01K 13/00 | 374/143 |
| 2014/0009151 A1* | 1/2014 | Van Helvoort | G01R 33/34023 | 324/322 |
| 2014/0053576 A1* | 2/2014 | Lose | H01F 6/04 | 62/51.1 |
| 2015/0042339 A1* | 2/2015 | Lazar | G01R 33/3856 | 324/318 |
| 2015/0047377 A1* | 2/2015 | Hamasaki | H01F 6/04 | 62/115 |
| 2015/0153428 A1* | 6/2015 | Chen | G01R 33/3804 | 324/318 |
| 2016/0291104 A1* | 10/2016 | Tsuda | G01R 33/3804 | |
| 2017/0045590 A1* | 2/2017 | Takai | G01R 33/022 | |
| 2017/0082708 A1* | 3/2017 | Liu | H01F 6/06 | |
| 2017/0139023 A1* | 5/2017 | Kusahara | G01R 33/4816 | |
| 2018/0035957 A1* | 2/2018 | Liu | A61B 6/037 | |
| 2018/0045796 A1* | 2/2018 | Schauwecker | G01R 33/30 | |
| 2018/0321344 A1* | 11/2018 | Kimmlingen | G01R 33/543 | |
| 2019/0011511 A1* | 1/2019 | Stainsby | G01R 33/3815 | |
| 2019/0072624 A1* | 3/2019 | Biber | G01R 33/583 | |
| 2019/0086276 A1* | 3/2019 | Delgoshaei | F24F 11/30 | |
| 2019/0310333 A1* | 10/2019 | Ham | G01R 33/3403 | |
| 2019/0311332 A1* | 10/2019 | Turney | G06Q 10/20 | |

* cited by examiner

SYSTEM AND METHOD FOR MONITORING COOLING SYSTEM

CROSS-REFERENCE TO RELATED APPLICATION(S)

The present application claims priority to and the benefit of U.S. Provisional Application No. 62/679,701, filed Jun. 1, 2018, entitled "DIFFERENTIALS", the entire content of which is incorporated herein by reference.

FIELD

One or more aspects of embodiments according to the present disclosure relate to cooling systems, and more particularly to a system and method for monitoring a cooling system.

BACKGROUND

Temperature-sensitive systems, such as magnetic resonance imaging systems, may have stringent cooling requirements to maintain proper operation or to avoid damage. For example, a magnetic resonance imaging system may include a multi-stage cryogenic cooling system employed to keep a superconducting magnet at sufficiently low temperature to maintain superconductivity. Various faults may occur in such a cooling system; such faults may, in some instances, gradually become more severe, eventually causing the system to shut down.

As such, it may be advantageous to be able to detect and diagnose faults, and, where possible, to detect and diagnose them well before a system shutdown results.

SUMMARY

According to an embodiment of the present invention, there is provided an apparatus for monitoring a cooling system including a chiller and a heat exchange process connected to the chiller by a coolant supply line and by a coolant return line, the apparatus including: a first temperature sensor, for measuring a coolant temperature in the coolant supply line; a second temperature sensor, for measuring a coolant temperature in the coolant return line; and a readout circuit, for monitoring respective temperatures sensed by first temperature sensor and the second temperature sensor.

In some embodiments, the first temperature sensor is secured to the coolant supply line, and the second temperature sensor is secured to the coolant return line.

In some embodiments: the first temperature sensor is secured to the coolant supply line within 60 inches of the heat exchange process, or the second temperature sensor is secured to the coolant return line within 60 inches of the heat exchange process.

In some embodiments: a thermal time constant for coolant temperature fluctuations, at the first temperature sensor, is less than 5 minutes, or a thermal time constant for coolant temperature fluctuations, at the second temperature sensor, is less than 5 minutes.

In some embodiments: the first temperature sensor is secured to a metal portion of the coolant supply line, or the second temperature sensor is secured to a metal portion of the coolant return line.

In some embodiments, the readout circuit includes a processing circuit configured to: perform a first temperature sensing operation with the first temperature sensor, during an interval of time; and perform a second temperature sensing operation with the second temperature sensor, during the interval of time.

In some embodiments, the processing circuit is further configured to display, on a display, a first temperature value and a second temperature value.

In some embodiments, the first temperature value is a difference between a temperature measured in the first temperature sensing operation, and a temperature measured in the second temperature sensing operation.

In some embodiments, the second temperature value is the temperature measured in the first temperature sensing operation.

In some embodiments, the apparatus further includes a battery-based power supply for providing power to the processing circuit.

In some embodiments, the apparatus further includes a cellular modem connected to the processing circuit.

In some embodiments, the readout circuit includes a processing circuit configured to: perform a plurality of temperature sensing operations with the first temperature sensor, during an interval of time; and perform a plurality of temperature sensing operations with the second temperature sensor, during the interval of time.

In some embodiments, the processing circuit is further configured to display, on a display, a first temperature history and a second temperature history.

In some embodiments, the heat exchange process is a compressor of a helium refrigerator for a superconducting magnet of a magnetic resonance imaging machine.

In some embodiments, the apparatus further includes a flow meter for measuring fluid flow in the coolant supply line or the coolant return line.

According to an embodiment of the present invention, there is provided an apparatus for monitoring a cooling system including a chiller and a heat exchange process connected to the chiller by a coolant supply line and a coolant return line, the apparatus including: a first temperature sensor, secured to the coolant supply line; and a second temperature sensor, secured to the coolant return line.

In some embodiments: the first temperature sensor is secured to the coolant supply line within 60 inches of the heat exchange process, or the second temperature sensor is secured to the coolant return line within 60 inches of the heat exchange process.

In some embodiments: a thermal time constant for coolant temperature fluctuations, at the first temperature sensor, is less than 5 minutes, or a thermal time constant for coolant temperature fluctuations, at the second temperature sensor, is less than 5 minutes.

In some embodiments, the apparatus further includes: a processing circuit; a battery-based power supply, connected to the processing circuit; and a cellular modem connected to the processing circuit, the processing circuit being configured to: perform a first temperature sensing operation with the first temperature sensor, during an interval of time; perform a second temperature sensing operation with the second temperature sensor, during the interval of time; and to display, on a display: a difference between a temperature measured in the first temperature sensing operation and a temperature measured in the second temperature sensing operation, and the temperature measured in the first temperature sensing operation.

BRIEF DESCRIPTION OF THE DRAWINGS

These and other features and advantages of the present disclosure will be appreciated and understood with reference to the specification, claims, and appended drawings wherein:

DETAILED DESCRIPTION

The detailed description set forth below in connection with the appended drawings is intended as a description of exemplary embodiments of a system and method for monitoring a cooling system provided in accordance with the present disclosure and is not intended to represent the only forms in which the present disclosure may be constructed or utilized. The description sets forth the features of the present disclosure in connection with the illustrated embodiments. It is to be understood, however, that the same or equivalent functions and structures may be accomplished by different embodiments that are also intended to be encompassed within the scope of the disclosure. As denoted elsewhere herein, like element numbers are intended to indicate like elements or features.

Figure 1:
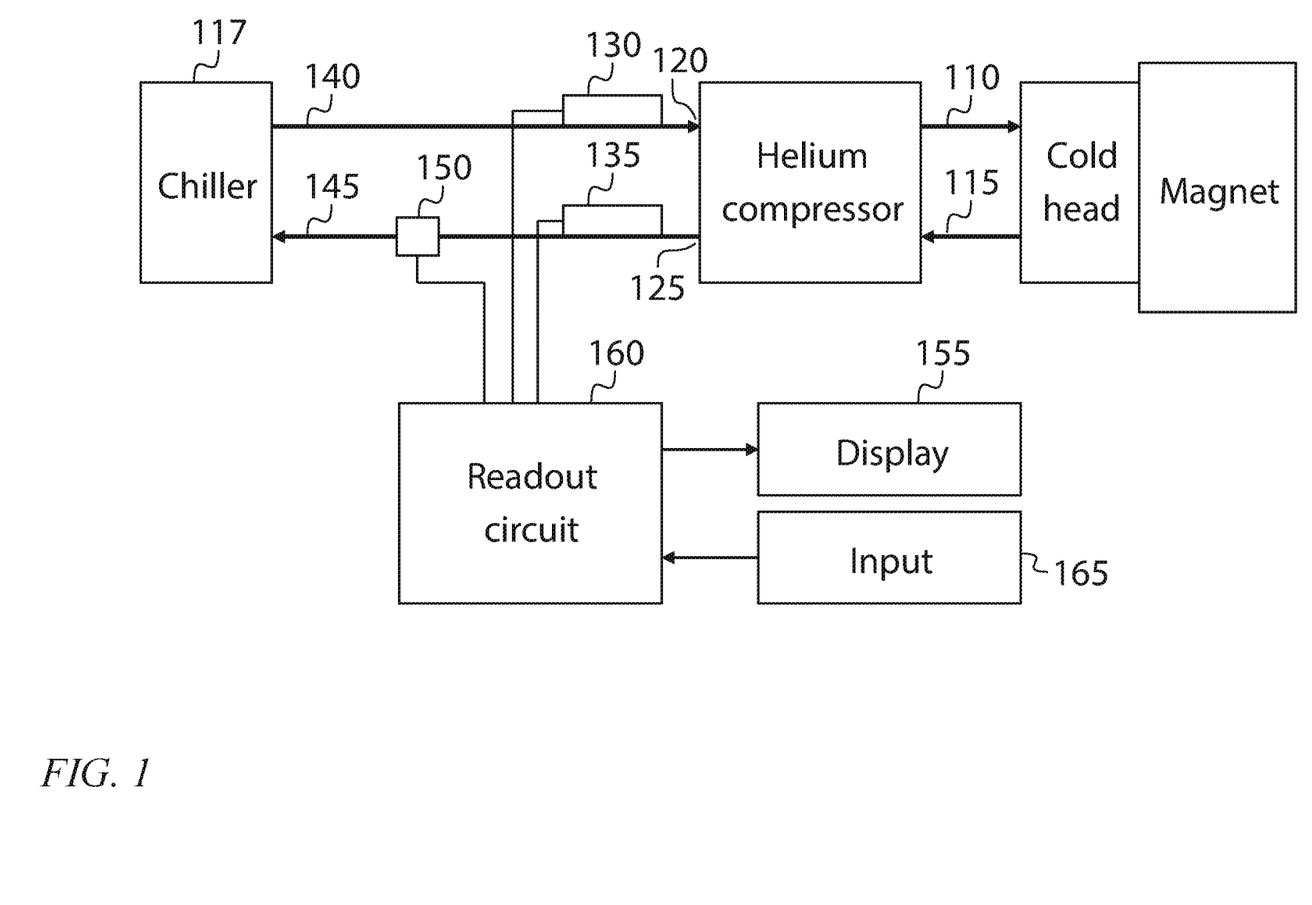
FIG. 1 is a block diagram of system for monitoring a cooling system, according to an embodiment of the present disclosure.

Referring to FIG. 1, in some embodiments, a cooling system for a magnet (e.g., a superconducting magnet) in an MRI system includes a helium compressor that compresses and cools a mixture of helium gas and oil, and feeds it, through an outlet, or "helium outlet" 110, to a cold head. In the cold head, the compressed helium is caused to do work as it expands within a set of displacers; as a result of doing this work the helium cools further, and is used to cool the magnet to cryogenic temperatures sufficiently low to keep the conductors of the magnet superconducting. After flowing through the cold head, the helium and oil mixture returns, through an inlet, or "helium inlet" 115, of the helium compressor, to the helium compressor.

The helium compressor is in turn cooled by coolant that it receives from a coolant source, such as a chiller 117, through an inlet coolant line 140, at a coolant inlet 120, and which after passing through the helium compressor leaves the helium compressor through an outlet coolant line 145, at a coolant outlet 125. An inlet temperature sensor 130 may be secured to the inlet coolant line, and an outlet temperature sensor 135 may be secured to the outlet coolant line, the two sensors being part of a monitoring system for the cooling system, as discussed in further detail below. The inlet coolant line 140 may be insulated, and carries chilled coolant from the chiller 117 to the helium compressor. The outlet coolant line 145 may also be insulated, and carries return coolant from the helium compressor to the chiller 117.

The subsystem being cooled by the coolant, e.g., the helium compressor, may be referred to as the "heat exchange process". As used herein, a "heat exchange process" is any heat source that may be connected to, and cooled by, a coolant source. Some embodiments may be used with other types of heat exchange processes, e.g., linear accelerators or CAT scan machines. In some embodiments the coolant source is not a dedicated chiller 117 as shown in FIG. 1 but is instead, for example, a large scale refrigeration system also supplying coolant to other heat exchange processes, such as other MRI systems, or an air conditioning system for a building housing an MRI machine. The heat exchange process may require that the coolant temperature be within a certain range, and that the flow rate be in a certain range (which may depend on the temperature); the permissible combinations of flow rate and temperature may be called the "admissible range". For example, the inlet coolant temperature may be required to be between 4 degrees C. and 28 degrees C. and the coolant flow rate may be required to be less than 10 liters per minute, and greater than a linear function of temperature, the linear function having a value of 4 liters per minute at a temperature of 4 degrees C. and value of 7 liters per minute at a temperature of 28 degrees C.

The chiller may include a reservoir of coolant (which may be a mixture of, e.g., 30% ethylene glycol and 70% deionized water), a refrigerator, and a pump that circulates coolant from a coolant inlet of the chiller, through the reservoir (which may also act as a heat exchanger of the refrigerator), through a coolant filter, through the helium compressor, and back to the chiller. A temperature sensor (e.g., on the reservoir) may be used to control the refrigerator of the chiller, so that the chiller cycles on (e.g., the refrigerator of the chiller cycles on) when the temperature of the reservoir exceeds an upper threshold, and the chiller cycles off (e.g., the refrigerator of the chiller cycles off) when the temperature of the reservoir falls below a lower threshold.

The inlet coolant line 140 may include a fluid-carrying line surrounded by a layer of insulation. The fluid carrying line may be a hose, tube, or pipe (e.g., composed of metal or of reinforced (or unreinforced) polymer (e.g., plastic or an elastomer)). The insulation may be flexible or rigid foam or fiber insulation. The inlet temperature sensor 130 may be secured, inside the layer of insulation, e.g., with adhesive tape, to the fluid carrying line. A thermal compound or thermal pad may be used between the inlet temperature sensor 130 and the fluid carrying line to establish good thermal contact between them. The outlet coolant line 145 may be of a similar construction, and the outlet temperature sensor 135 may be installed within it in an analogous fashion.

In some embodiments, the inlet temperature sensor 130 and the outlet temperature sensor 135 are installed near the heat exchange process, e.g., within 10 inches or within 60 inches of the heat exchange process, for a poorly insulated line, or at a greater distance, e.g., up to 500 feet, for a well-insulated line, and they are installed such that the thermal conductivity of the thermally conductive path between the coolant and each temperature sensor is relatively high (e.g., greater than 0.01 W/K). The thermal conductivity may be increased by securing the inlet temperature sensor 130 and the outlet temperature sensor 135 to a metal portion of the inlet coolant line 140 and the outlet coolant line 145, respectively.

This installation approach may improve the quality of the temperature measurements, e.g., it may improve the signal to noise ratio for sensing, e.g., temperature fluctuations at the outlet of the heat exchange process. If, for example, the outlet temperature sensor 135 were instead installed at a location on the outlet coolant line 145 that is distant from the heat exchange process, and the outlet coolant line were poorly insulated, then the effect of temperature fluctuations at the outlet of the heat exchange process would be attenuated as a result of heat being conducted out of the outlet coolant line 145 into the air in the room, and it is possible that significant noise would be introduced as a result of fluctuations in room temperature. Further, (as discussed in further detail below) if the thermal conductivity of the thermally conductive path between the coolant and each temperature sensor is relatively low, then the combination of the thermal resistance of the conductive path and the heat capacity of the temperature sensor may act as a low-pass filter, suppressing relatively high-frequency signals such as those caused by the chiller cycling on and off. As such, each of the inlet temperature sensor 130 and the outlet temperature sensor 135 may be installed (e.g., on a metal portion of the respective coolant line, using a thermal compound, and without other thermally massive parts (such as a metal clamp) in contact with the temperature sensor) such that the thermal time constant, at the temperature sensor, for coolant temperature fluctuations, is less than e.g., 1 minute or 5 minutes (e.g., such that the thermal time constant is between 0.1 minutes and 100.0 minutes).

Each temperature sensor may be, for example, a Dallas Semiconductor DS18B20 temperature sensor packaged in a waterproof (e.g., a substantially cylindrical stainless steel) housing. The analog signals from the temperature sensors may be amplified and filtered and periodically sampled and converted to digital form with an analog to digital converter. The interval between successive samples may be as short as the response time of the sensors, or considerably longer, corresponding for example to the shortest time scale on which significant temperature changes are expected to take place. The interval between successive samples may be between 0.1 second and 1000.0 seconds, and it may be, for example, 0.1 seconds, 1 second, 10 seconds, or 100 seconds. In some embodiments, sensor assemblies including sensors and analog to digital converters, and producing digital (e.g., 1-wire) output signals (e.g., model OW-TEMP-S3-12 temperature probes, available from embeddeddatasystems.com) may be used.

In some embodiments, one or more flow meters 150 may be included in the system, e.g., on the outlet coolant line 145 (as shown in FIG. 1) or on the inlet coolant line 140, or in the heat exchange process, or in the cooler. Such a flow meter may be used to calculate (as the product of the temperature difference and the flow rate) the total rate at which heat is removed from the heat exchange process by the coolant. The flow meter 150 may have a paddle-wheel sensor, an infrared sensor, a Doppler sensor, or a magnetic sensor, and it may be selected to be capable of measuring a flow rate of up to five gallons per minute, in a pipe with an inside diameter of about ⅜ inch.

The digital data, which may include two sequences (one for each of the two temperature sensors) of periodic temperature measurements, may then be stored for later analysis or sent in a stream to a user device such as a display. The data may be displayed to the user as a graph with two traces, each trace showing the history of a respective one of the two temperatures. From such a graph a user may observe changes in the temperatures and, from them, assess the status of the magnet cooling system and diagnose potential problems. In some embodiments, the temperature data may be displayed in a "dashboard view" showing only, e.g., the numerical values of the most recent readings from the inlet temperature sensor 130 and the outlet temperature sensor 135, or (i) the most recent reading from the inlet temperature sensor 130 and (ii) the difference between the most recent reading from the outlet temperature sensor 135 and the inlet temperature sensor 130. Each value displayed (in a graph, or as a numerical value), may be a linear combination of a temperature reading from the inlet temperature sensor 130 and a temperature reading from the outlet temperature sensor 135. For example, one such linear combination may be (as mentioned above) the difference between the most recent reading from the outlet temperature sensor 135 and the inlet temperature sensor 130. Other possibilities for such linear combinations include (i) the temperature reading from the inlet temperature sensor 130 and (ii) the temperature reading from the outlet temperature sensor 135. If a flow meter 150 is present, the system may also display (as a numerical value or as a graph) the flow rate, or a quantity derived from the flow rate and the measured temperatures, such as the total rate at which heat is removed from the heat exchange process by the coolant.

Figure 2A:
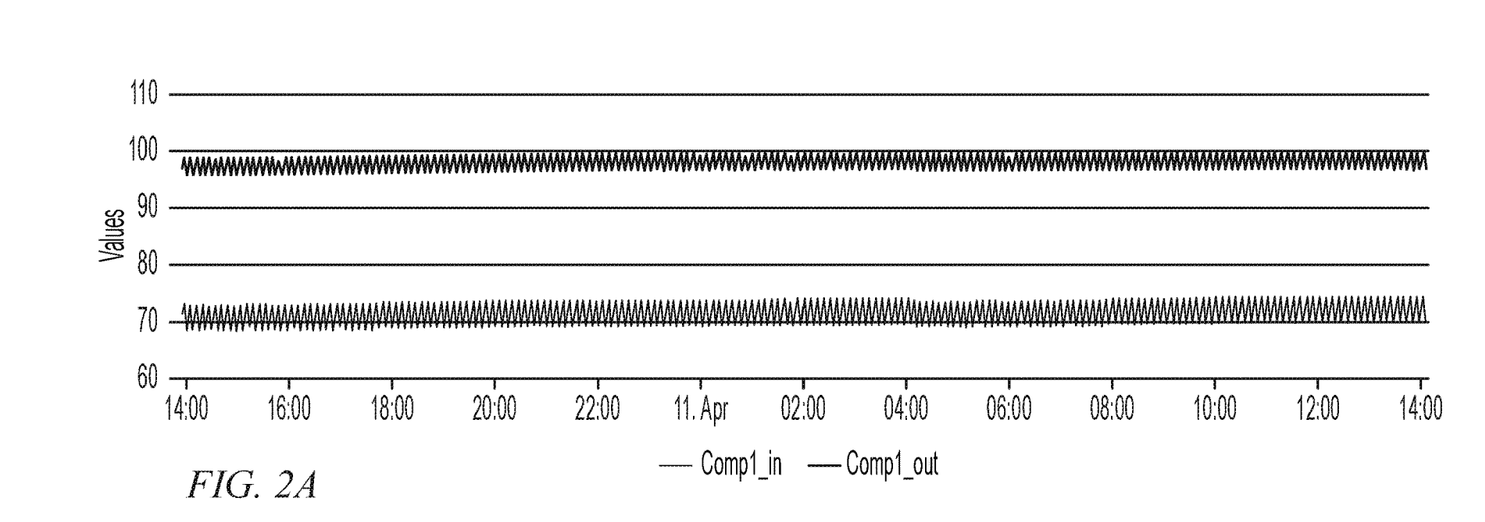
FIG. 2A is a graph of temperatures, according to an embodiment of the present disclosure.

FIG. 2A is a graph of the temperature at the helium compressor coolant inlet ("Comp1_in"; the lower temperature history shown) and at the helium compressor coolant outlet ("Comp1_out"; the upper temperature history shown) during normal operation, in some embodiments. During normal operation, the two temperatures may, on average, each be relatively constant, and may decrease together when the refrigerator in the chiller 117 cycles on, and increase together when the refrigerator in the chiller 117 cycles off. The normal inlet temperature may be in the range of 40 degrees (Fahrenheit) to 82 degrees, and the normal temperature difference may be between 10 and 25 degrees. Each temperature may, in normal operation, fluctuate (as shown) by about 5 degrees (e.g., +/−2.5 degrees) as the refrigerator in the chiller 117 cycles on and off. A graph such as that of FIG. 2A may be displayed on a display 155 (FIG. 1) by a suitable readout circuit 160.

The duty cycle, in the graph of FIG. 2A, is about 50% (the upward-sloping portions and downward-sloping portions being about equally steep), implying that about one half of the cooling capacity of the refrigerator of the chiller is being utilized. If the duty cycle increases, it may be an indication that the reserve cooling capacity of the refrigerator is decreasing. For example, if the temperature of the ambient air that the chiller uses for cooling increases, an increase in the duty cycle may be observed, as the rate at which the refrigerator is able to extract heat from the coolant is reduced, and the time required to cool the reservoir from the upper threshold to the lower threshold increases. As such, an observed increase in duty cycle may be used to infer a loss of cooling capacity reserve. Further, a trend in the duty cycle may be used to predict when the duty cycle will reach 100% and the chiller outlet temperature will continue to increase even when the chiller refrigerator cycles on. The ability to determine the chiller duty cycle in the coolant temperature (e.g., from the durations or slopes of the upward-sloping and downward-sloping portions) may require a relatively good thermal contact between the temperature sensors and the coolant (so that the upward-sloping portions may be distinguishable from the downward-sloping portions in at least one of the temperature histories), because (as mentioned above) a relatively poor thermal contact may cause low-pass filtering of the temperature measurement, which may have the effect of smoothing the temperature traces (as may be seen in FIGS. 2B-2D, discussed in further detail below).

Figure 2B:
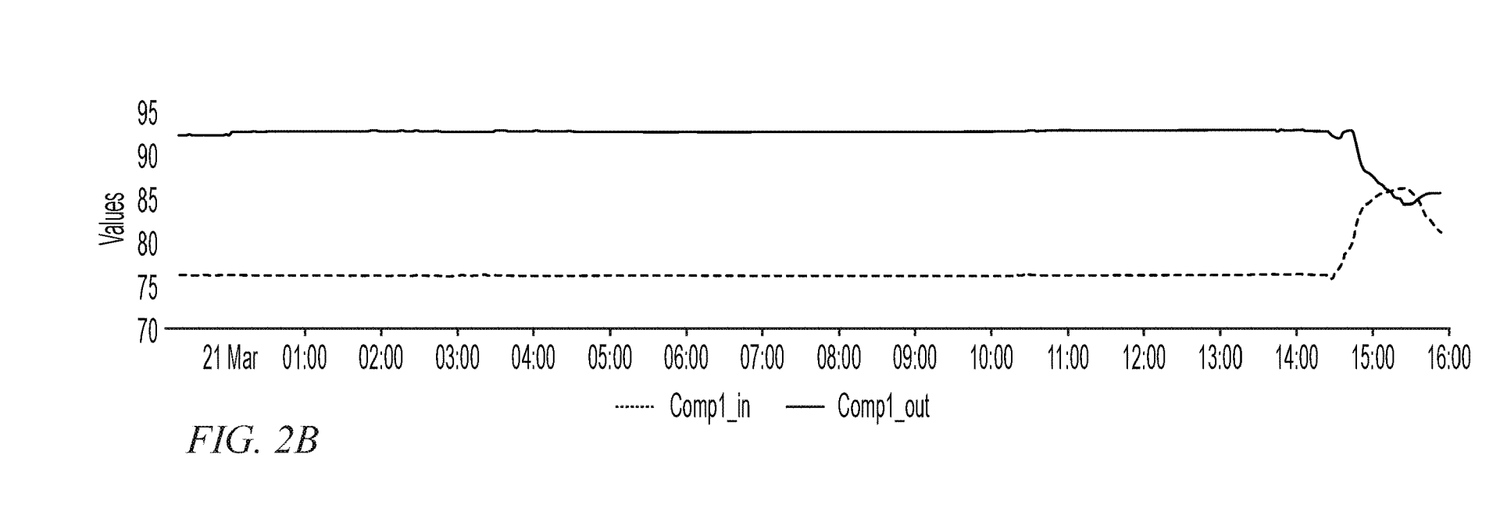
FIG. 2B is a graph of temperatures, according to an embodiment of the present disclosure.

FIG. 2B shows the temperature history that may be observed if a power outage causes the helium compressor and the chiller to be shut off simultaneously (at about 14:30 in the graph of FIG. 2B). In such a situation, the coolant return line from the heat exchange process may begin to cool, because the heat exchange process is no longer generating, heat, and the coolant inlet to the heat exchange process may begin to warm, because the chiller is no longer supplying chilled coolant. If the power failure persists for a long time, both temperatures would be expected to approach ambient temperature (e.g., room temperature). The change in direction visible in both histories at 15:30 may correspond to power being restored at that time.

Figure 2C:
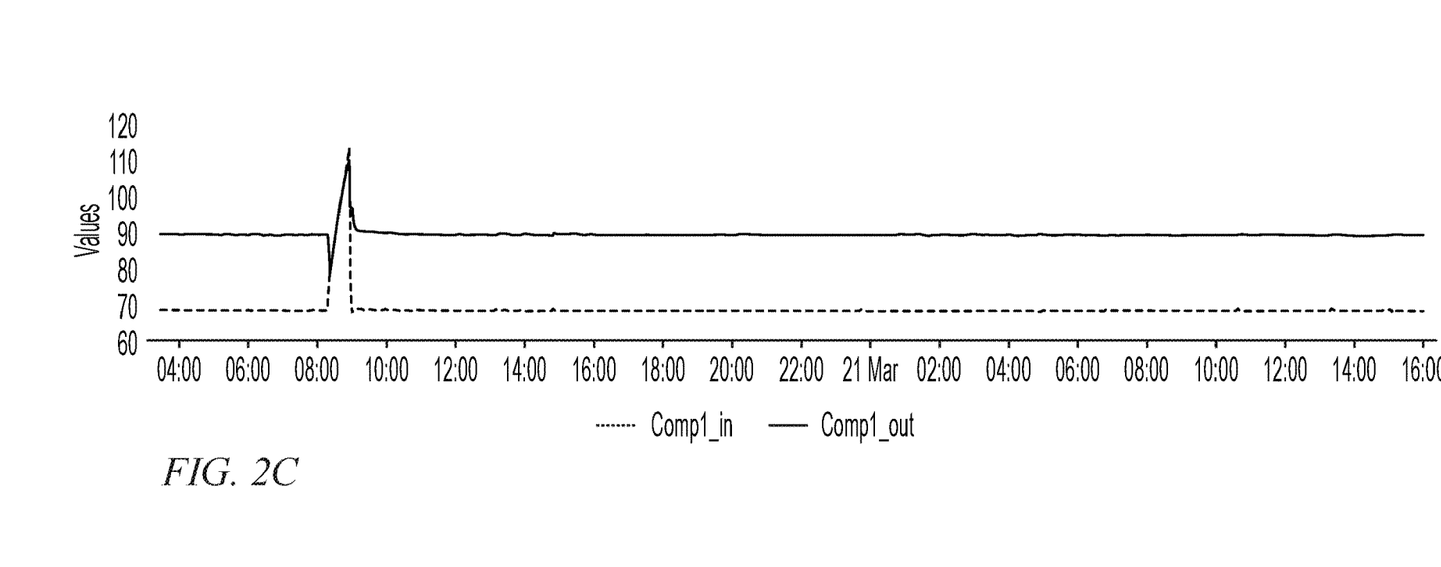
FIG. 2C is a graph of temperatures, according to an embodiment of the present disclosure.

FIG. 2C shows the temperature history that may be observed if the refrigerator of the chiller shuts down (while the pump continues to operate) and the helium compressor shuts down at nearly the same time (e.g., at about 8:10) when the compressor detects that the temperature at the coolant inlet has fallen outside of the admissible range. In FIG. 2C, normal operation is then restored at about 9:00.

Figure 2D:
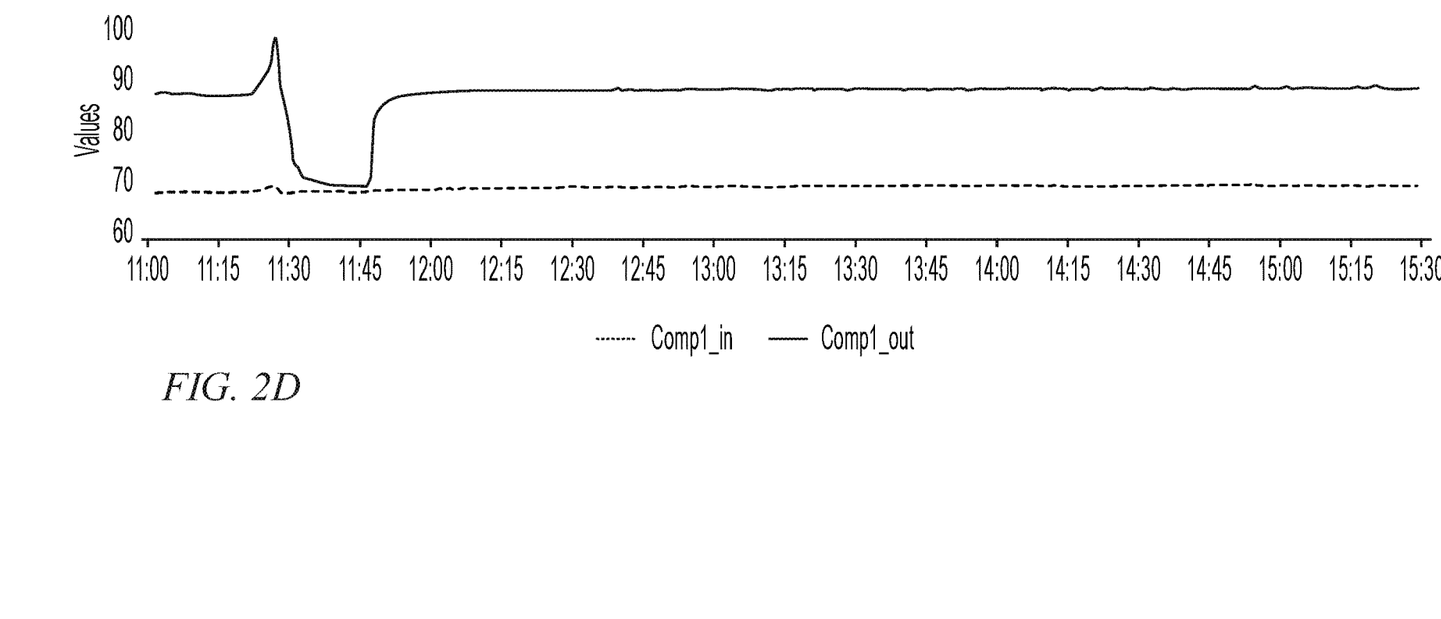
FIG. 2D is a graph of temperatures, according to an embodiment of the present disclosure.

FIG. 2D shows the temperature history that may be observed if the helium compressor shuts down, e.g., as a result of a reduction in coolant flow, and a resultant increase in the outlet coolant temperature of the helium compressor (e.g., at about 11:25, in the graph shown). The coolant inlet temperature is substantially unchanged, being controlled by the internal temperature controller of the chiller, while the temperature difference drops to nearly zero, as the helium compressor ceases to heat the coolant flowing through it.

As mentioned above, the periodic temperature fluctuations caused by the chiller cycling on and off are not visible in FIGS. 2B-2D, possibly because the thermal resistance between the coolant and each temperature sensor, combined with the thermal inertia of the temperature sensor and its surroundings, act as a thermal low-pass filter.

Other changes in the condition of the cooling system may also be detected, based on the temperature measurements. For example, a reduction in the coolant flow rate may cause the temperature difference to increase, as the substantially constant heat load from the helium compressor is carried away by a reduced flow of fluid. The reduction in coolant flow rate may in turn be a symptom of several potential causes, including a clogged filter or heat exchanger in the chiller, a clogged heat exchanger in the helium compressor, a pinched hose between the chiller and the helium compressor, the chiller being low on coolant (which may cause the chiller to shut down, if it is configured to shut down when the level in the reservoir drops below a threshold level, or which may cause the chiller pump to lose efficiency as it pumps a mixture of coolant and air), or a chiller pump failure. An improper coolant solution (e.g., a solution containing too little ethylene glycol) may fail to adequately inhibit bacterial growth and may result in clogging of the filter or heat exchanger in the chiller, or clogging of any other element having one or more small passages carrying coolant. As such, an increasing temperature difference may be an indication of reduced coolant flow, caused, for example, by clogging.

Excessive coolant flow may cause the temperature difference to decrease. Excessive coolant flow may be a symptom of a flow regulator failure in a system using an oversized chiller (e.g., using a facility-scale cooling plant, as mentioned above). Excess coolant flow may reduce the efficiency of the helium compressor. A failure of the refrigerator in the chiller may cause both temperatures to increase together, initially, until the helium compressor inlet temperature increases sufficiently to cause the helium compressor to shut down.

If the helium compressor or the cold head fails while the chiller continues to operate normally, the heat load will fall to zero, and both temperatures will be seen to drop rapidly, until the refrigerator in the chiller cycles off. The flow meter, which may be used, as mentioned above, to calculate the total rate at which heat is removed from the heat load by the coolant, may be helpful in detecting such a condition.

It may be seen from the foregoing examples that a temperature measuring system as described herein may be used to diagnose potential problems in a cooling system, and to derive information about the operating conditions of such a cooling system.

Figure 3:
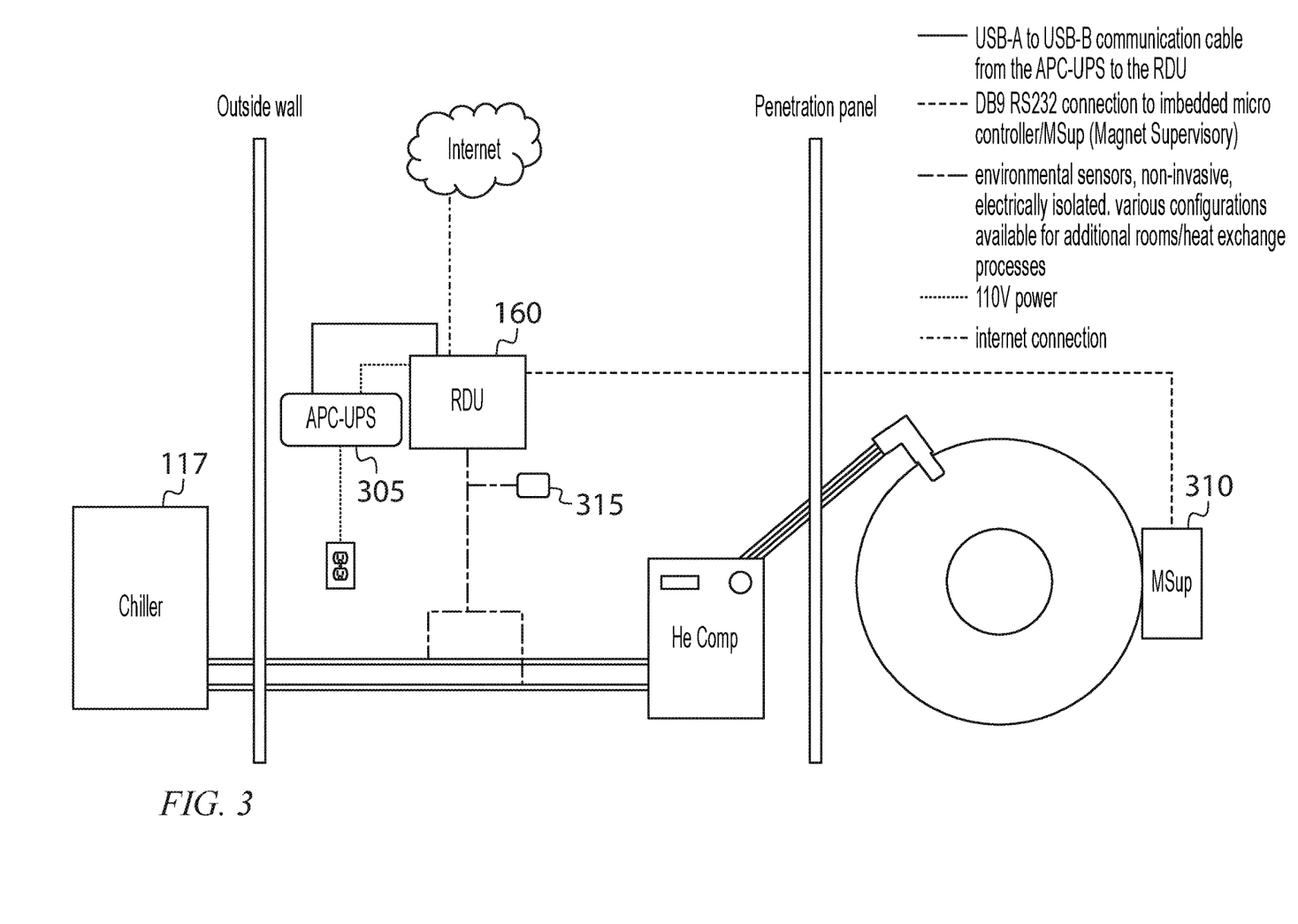
FIG. 3 is a block diagram of system for monitoring a cooling system, according to an embodiment of the present disclosure.

In some embodiments, the system and method for monitoring a cooling system may include a battery-based power supply (or "uninterruptible power supply" (UPS)) 305 for the readout circuit 160 (or "remote diagnostic unit" (RDU)), as shown in FIG. 3.

In some embodiments, a mobile MRI system is installed on a trailer with a 480 V generator for powering the helium compressor and the chiller. When the MRI system is operating, the trailer may be connected to shore power, which may include 480 V power for the helium compressor and the chiller, and 110 V power for powering the readout circuit 160. The 480 V generator may run when the trailer is in transit, so that the liquid helium bath may be maintained. Power at 110 V, for use by the readout circuit 160, may not be available from the 480 V generator on the trailer. To be able to continue monitoring the condition of the magnet cooling system during transit, the battery-based power supply may be charged while the system is connected to shore power, and battery power may then be used to power the readout circuit 160 during transit. Communications to a monitoring center may be maintained by a via cellular modem in (or connected to) the readout circuit 160, and via the Internet, to which the cellular modem may provide a connection.

The readout circuit 160 (FIG. 1) may include a processing circuit configured to receive temperature readings from the temperature sensors (and, in some embodiments, from other sensors such as the monitor 315) and display the results (as mentioned above) on a display. The display may be, for example, a display on a web client computer connected through the internet to the processing circuit receiving the temperature readings. One or more user input devices 165 (e.g., a keyboard and a mouse) may be connected to the readout circuit 160 (or to a remote web client computer) to allow a user to specify what data are to be displayed and to select a display format. The readout circuit 160 may be a motherboard, or a desktop or laptop computer with suitable interface cards for connecting to the temperature sensors, for example.

The term "processing circuit" is used herein to mean any combination of hardware, firmware, and software, employed to process data or digital signals. Processing circuit hardware may include, for example, application specific integrated circuits (ASICs), general purpose or special purpose central processing units (CPUs), digital signal processors (DSPs), graphics processing units (GPUs), and programmable logic devices such as field programmable gate arrays (FPGAs). In a processing circuit, as used herein, each function is performed either by hardware configured, i.e., hard-wired, to perform that function, or by more general purpose hardware, such as a CPU, configured to execute instructions stored in a non-transitory storage medium. A processing circuit may be fabricated on a single printed circuit board (PCB) or distributed over several interconnected PCBs. A processing circuit may contain other processing circuits; for example a processing circuit may include two processing circuits, an FPGA and a CPU, interconnected on a PCB.

As used herein, the word "or" is inclusive, so that, for example, "A or B" means any one of (i) A, (ii) B, and (iii) A and B. Any numerical range recited herein is intended to include all sub-ranges of the same numerical precision subsumed within the recited range. For example, a range of "between 1.0 and 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein.

Although exemplary embodiments of a system and method for monitoring a cooling system have been specifically described and illustrated herein, many modifications and variations will be apparent to those skilled in the art. Accordingly, it is to be understood that a system and method for monitoring a cooling system constructed according to principles of this disclosure may be embodied other than as specifically described herein. The invention is also defined in the following claims, and equivalents thereof.

What is claimed is:

1. An apparatus for monitoring a cooling system comprising a chiller and a heat exchange process connected to the chiller by a coolant supply line and by a coolant return line, the apparatus comprising:
a first temperature sensor, for measuring a coolant temperature in the coolant supply line;
a second temperature sensor, for measuring a coolant temperature in the coolant return line; and
a readout circuit, for monitoring respective temperatures sensed by the first temperature sensor and the second temperature sensor,
wherein:
the coolant return line is configured to carry coolant from the heat exchange process to the chiller,
the readout circuit comprises a processing circuit configured to:
perform a first temperature sensing operation with the first temperature sensor, during an interval of time;
perform a second temperature sensing operation with the second temperature sensor, during the interval of time; and
display, on a display, a first temperature value and a second temperature value, and
the first temperature value is a difference between a temperature measured in the first temperature sensing operation, and a temperature measured in the second temperature sensing operation.

2. The apparatus of claim 1, wherein the first temperature sensor is secured to the coolant supply line, and the second temperature sensor is secured to the coolant return line.

3. The apparatus of claim 2, wherein:
the first temperature sensor is secured to the coolant supply line within 60 inches of the heat exchange process, or
the second temperature sensor is secured to the coolant return line within 60 inches of the heat exchange process.

4. The apparatus of claim 2, wherein:
a thermal time constant for coolant temperature fluctuations, at the first temperature sensor, is less than 5 minutes, or
a thermal time constant for coolant temperature fluctuations, at the second temperature sensor, is less than 5 minutes.

5. The apparatus of claim 2, wherein:
the first temperature sensor is secured to a metal portion of the coolant supply line, or
the second temperature sensor is secured to a metal portion of the coolant return line.

6. The apparatus of claim 2, wherein the readout circuit comprises a processing circuit configured to:
perform a plurality of temperature sensing operations with the first temperature sensor, during an interval of time; and
perform a plurality of temperature sensing operations with the second temperature sensor, during the interval of time.

7. The apparatus of claim 6, wherein the processing circuit is further configured to display, on a display, a first temperature history and a second temperature history.

8. The apparatus of claim 1, wherein the second temperature value is the temperature measured in the first temperature sensing operation.

9. The apparatus of claim 1, further comprising a battery-based power supply for providing power to the processing circuit.

10. The apparatus of claim 9, further comprising a cellular modem connected to the processing circuit.

11. The apparatus of claim 1, wherein the heat exchange process is a compressor of a helium refrigerator for a superconducting magnet of a magnetic resonance imaging machine.

12. An apparatus for monitoring a cooling system comprising a chiller and a heat exchange process connected to the chiller by a coolant supply line and a coolant return line, the apparatus comprising:
a first temperature sensor, secured to the coolant supply line;
a second temperature sensor, secured to the coolant return line;
a processing circuit,
the processing circuit being configured to:
perform a first temperature sensing operation with the first temperature sensor, during an interval of time;
perform a second temperature sensing operation with the second temperature sensor, during the interval of time; and
to display, on a display:
a difference between a temperature measured in the first temperature sensing operation and a temperature measured in the second temperature sensing operation, and
the temperature measured in the first temperature sensing operation,
wherein the coolant return line is configured to carry coolant from the heat exchange process to the chiller.

13. The apparatus of claim 12, wherein:
the first temperature sensor is secured to the coolant supply line within 60 inches of the heat exchange process, or
the second temperature sensor is secured to the coolant return line within 60 inches of the heat exchange process.

14. The apparatus of claim 12, wherein:
a thermal time constant for coolant temperature fluctuations, at the first temperature sensor, is less than 5 minutes, or
a thermal time constant for coolant temperature fluctuations, at the second temperature sensor, is less than 5 minutes.

15. The apparatus of claim 12, further comprising:
a processing circuit; and a battery-based power supply, connected to the processing circuit.

\* \* \* \* \*